US00PP08319P

United States Patent [19]

Dahlqvist

[11] Patent Number: Plant 8,319

[45] Date of Patent: Jul. 27, 1993

[54] POINSETTIA PLANT 'LILO WHITE'

[75] Inventor: Kjell-Ingvar Dahlqvist, Höllviken, Sweden

[73] Assignee: Paul Ecke Ranch, Inc., Encinitas, Calif.

[21] Appl. No.: 747,194

[22] Filed: Aug. 19, 1991

[51] Int. Cl.[5] ..... A01H 5/00

[52] U.S. Cl. ..... Plt./86.2

[58] Field of Search ..... Plt. 86.1, 86.2, 86.3, Plt./86.4

*Primary Examiner*—James R. Feyrer

*Attorney, Agent, or Firm*—Arnold, White & Durkee

[57] ABSTRACT

Poinsettia 'Lilo White' is a new cultivar, distinguished by creamy white bracts and intense dark green foliage with self-branching characteristics. 'Lilo White' is a color sport of the dark red bracted 'Lilo' (U.S. Plant Pat. No. 6694) with the same flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as an white sport of 'Lilo' (U.S. Plant Pat. No. 6694) in my greenhouse in Malmo, Sweden. It was selected because of its early flowering, self branching, white flower bracts and dark green foliage; traits which distinguish it from other poinsettia cultivars, and seem to make it a desirable plant for commercial greenhouse production. After selection, 'Lilo White' was vegetatively reproduced plant from stem cuttings for test purposes in Malmo, Sweden. By subjecting clones of this plant to successive generations of vegetative propagation, it was demonstrated that the distinctive characteristics of 'Lilo White' hold true from generation to generation.

The new plant was discovered among numerours cuttings cultivated from the parent 'Lilo'. One cutting produced a plant with white bracts which were distinct from the red bracts of the parent. The new plant also had stronger roots than 'Lilo', matured to a height about 2 cm taller than 'Lilo' and exhibited a better branching habit of 5–7 compared to the 4–7 branches typically observed with 'Lilo'.

The new cultivar 'Lilo White' was tested and found to be unusually resistant to epinasty. Epinasty refers to the drooping of bracts which often occurs during shipping of some poinsettia plants. Generally, epinasty resistance is tested by placing the plant in a shipping sleeve and observing any effects after a period of time in darkness. When tested for epinasty, 'Lilo White' showed a 2–3 week longer period of resistance to epinasty than the parent 'Lilo'.

DESCRIPTION OF THE PHOTOGRAPHS

Poinsettia 'Lilo White' is illustrated in the accompanying color photographs. The upper photo is a side view of a typical branched plant in full flower. The lower photo is a top view of the same plant showing flower and bract formation.

DESCRIPTION OF THE PLANT

The following is a detailed description of this new poinsettia as observed in Encinitas, Calif., U.S.A. during December 1990. Observations were recorded from flowering plants, grown as 1 branched plant per pot.

The pot was 14 cm. in diameter and 11 cm. in height. Color designations are compared to the 1987 edition of R.H.S. Colour Chart, first published in 1966 by The Royal Horticultural Society, London, England.

THE PLANT

Origin: Sport of 'Lilo' (U.S. Plant Pat. No. 6,694)

Classification:

*Botanic.*—*Euphorbia pulcherrima* Willd.

*Common name.*—Poinsettia.

*Cultivar name.*—'Lilo White'.

Form: Shrub.

Height: Medium.

Growth habit: As a single stemmed plant, upright and vigorous with many self-branching side shoots. The application of a chemical growth retardant may be needed to restrict height for commercial pot plant production. I observed a pinched plant with 8 strong branches, an overall height of 34 cm. and an overall width of 41 cm. The bract diameter of individual flowers was 24 cm.

Branching: Axillary branches will develop and terminate in a flower without pinching. However, it is usually desirable to pinch 'Lilo White' and remove all terminal dominance. Then, all axillary branches will develop uniformly and at a faster rate.

Growth rate: Rooting of stem cuttings occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The leaves are of medium size, leaf blades typically being about 14–16 cm. long and about 9–11 cm. wide with leaf petioles about 5–6 cm. long.

*Leaf shape.*—Typical leaves are generally ovate with obtuse bases and acuminate tips. Leaf margins are entire or weakly lobed with 1 or 2 indentations on each side of the leaf blade.

*Color.*—Upper side — Dark green, darker than R.H.S. 147A. Under side — Green, between R.H.S. 147A and R.H.S. 147B.

*Retention.*—The foliage lasts extremely well even under low light intensities in the consumer's home.

Bracts: Generally there are 24–27 white bracts of various sizes subtending the cyathia. The primary bracts have blades typically 14–15 cm. long and 10–11 cm. wide with petioles about 2–4 cm. long.

*Shape.*—Bracts are mostly ovate to elliptic with acute bases and acuminate tips. Primary bracts are weakly lobed with 1 or 2 indentations on either side of the bract. Secondary bracts have entire margins.

*Color.*—Upper side — Creamy white, near R.H.S. 2D. Under side — Creamy white, near R.H.S. 2D.

Flowers: Generally, 18–21 cyathia (flowers) are present when the plant is in full bloom. Each cyathium is about 6–7 mm long and 5–6 mm wide, green in color, and fringed with yellow at the distal end. A yellow nectar cup protrudes from the side of each cyathium. The flower pedicel is also green and about 4–5 mm in length. The stamens protruding from the cyathia are white.

What is claimed is:

1. A new and distinct Poinsettia cultivar, substantially as herein shown and described, distinguished by its intense dark green foliage, creamy white bracts, self branching and resistance to epinasty.

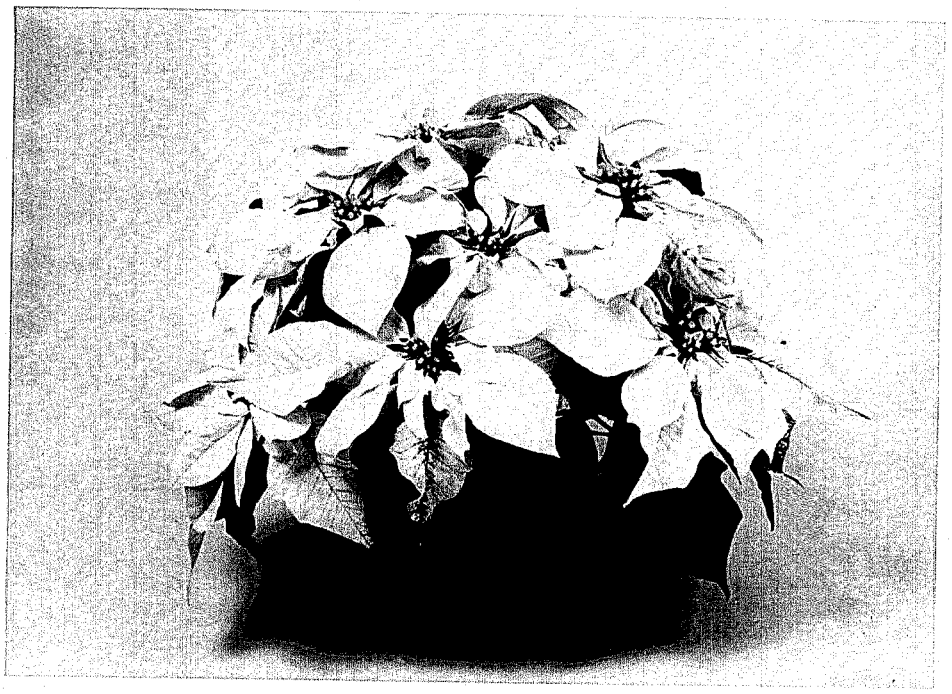
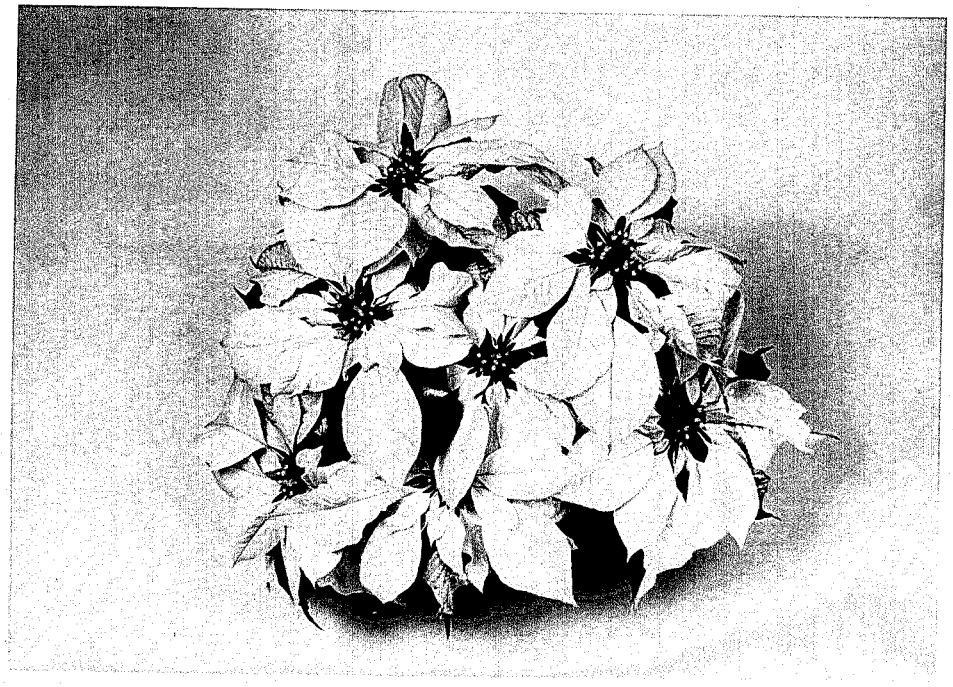

* * * * *